US011319268B2

(12) United States Patent
Chrisman et al.

(10) Patent No.: US 11,319,268 B2
(45) Date of Patent: May 3, 2022

(54) CONTINUOUS, CARBOHYDRATE TO ETHYLENE GLYCOL PROCESSES

(71) Applicant: Iowa Corn Promotion Board, Johnston, IA (US)

(72) Inventors: Ray Chrisman, Midland, MI (US); Donald Bunning, South Charleston, WV (US); Mark Nunley, Charleston, WV (US); Brooke Albin, Charleston, WV (US); Michael Bradford, Charleston, WV (US); Louis A. Kapicak, Cross Lanes, WV (US); David James Schreck, Lake City, MN (US)

(73) Assignee: Iowa Corn Promotion Board, Jackson, IA (US)

( * ) Notice: Subject to any disclaimer, the term of this patent is extended or adjusted under 35 U.S.C. 154(b) by 0 days.

(21) Appl. No.: 17/031,280

(22) Filed: Sep. 24, 2020

(65) Prior Publication Data

US 2021/0087125 A1    Mar. 25, 2021

Related U.S. Application Data

(60) Provisional application No. 62/905,068, filed on Sep. 24, 2019.

(51) Int. Cl.
| | |
|---|---|
| *C07C 29/132* | (2006.01) |
| *B01J 23/30* | (2006.01) |
| *B01J 19/00* | (2006.01) |
| *B01J 19/24* | (2006.01) |
| *C07C 29/17* | (2006.01) |
| *C07C 31/20* | (2006.01) |

(52) U.S. Cl.
CPC ........... *C07C 29/132* (2013.01); *B01J 19/004* (2013.01); *B01J 19/0033* (2013.01); *B01J 19/245* (2013.01); *B01J 23/30* (2013.01); *C07C 29/172* (2013.01); *B01J 2219/0004* (2013.01); *B01J 2219/00033* (2013.01); *B01J 2219/00243* (2013.01); *B01J 2523/69* (2013.01); *C07C 31/202* (2013.01)

(58) Field of Classification Search
CPC ... C07C 29/132; C07C 29/172; C07C 31/202; B01J 19/245; B01J 23/30; B01J 19/004; B01J 19/0033; B01J 2219/0004; B01J 2219/00243; B01J 2523/69; B01J 2219/00033
See application file for complete search history.

(56) References Cited

U.S. PATENT DOCUMENTS

| | | | |
|---|---|---|---|
| 3,077,379 A | 2/1963 | Pilloton | |
| 3,193,347 A | 7/1965 | Forward | |
| 3,472,613 A | 10/1969 | Hay et al. | |
| 3,857,929 A | 12/1974 | Quatrini et al. | |
| 4,200,765 A | 4/1980 | Goetz | |
| 4,279,870 A | 7/1981 | Natansohn | |
| 4,765,834 A | 8/1988 | Ananthapadmanabhan | |
| 6,841,085 B2 | 1/2005 | Werpy | |
| 7,038,094 B2 | 5/2006 | Werpy et al. | |
| 7,094,932 B2 | 8/2006 | Majerski | |
| 7,335,800 B2 | 2/2008 | Komplin | |
| 7,762,715 B2 | 7/2010 | Gordon | |
| 8,014,880 B2 | 9/2011 | Samardzija | |
| 8,222,462 B2 | 7/2012 | Kaines et al. | |
| 8,222,463 B2 | 7/2012 | Kaines | |
| 8,222,464 B2 | 7/2012 | Kaines | |
| 8,271,103 B2 | 9/2012 | Hendler | |
| 8,603,198 B2 | 12/2013 | Gordon | |
| 8,673,129 B2 | 3/2014 | Gordon | |
| 8,816,068 B2 | 8/2014 | Kuusisto | |
| 8,877,985 B2 | 11/2014 | Powell | |
| 8,981,135 B2 | 3/2015 | Gordon et al. | |
| 9,069,345 B2 | 6/2015 | McCready | |
| 9,302,965 B1 | 4/2016 | Van Der Heide et al. | |
| 9,440,897 B2 | 9/2016 | Lange et al. | |
| 9,447,347 B2 | 9/2016 | Chheda et al. | |
| 9,656,933 B2 | 5/2017 | Van Der Heide et al. | |
| 9,745,234 B2 | 8/2017 | Van Der Heide et al. | |
| 9,884,798 B2 | 2/2018 | Van Der Heide et al. | |
| 10,035,744 B2 | 7/2018 | Huizenga et al. | |
| 10,081,584 B2 | 9/2018 | Fischer et al. | |
| 10,093,602 B2 | 10/2018 | Van Der Heide et al. | |
| 10,125,071 B2 | 11/2018 | Van Der Heide et al. | |
| 10,131,600 B2 | 11/2018 | Van Der Waal et al. | |

(Continued)

FOREIGN PATENT DOCUMENTS

| | | |
|---|---|---|
| CN | 102643165 | 8/2012 |
| NL | 2014119 A | 9/2016 |

(Continued)

OTHER PUBLICATIONS

Guan, W et al., "Extraction of tungsten from simulated autoclave-soda leaching liquor of scheelite with quatemary ammonium salt. Zhongguo Youse Jinshu Xuebao/Chinese Journal of Nonferrous Metals", 2011, pp. 1756-1762, vol. 21.

Ismail et al., "Aqueous-Only, Green Route to Self-Healable, UV-Resistant, and Electrically Conductive Polyurethane/Graphene/Lignin Nanocomposite Coatings", "ACS Sustainable Chem. Eng.", Feb. 15, 2017, pp. 3148-3157, vol. 5.

Ke, Z.-H et al., "Research on tungsten extraction from alkali sodium tungstate solution with quatemary ammonium salt. Rare Metals and Cemented Carbides", 2012, pp. 14, vol. 40.

(Continued)

*Primary Examiner* — Jafar F Parsa

(74) *Attorney, Agent, or Firm* — Dentons Davis Brown, PC; Matthew Coryell

(57) ABSTRACT

By this invention processes are provided for the conversion of carbohydrate to ethylene glycol by retro-aldol catalysis and sequential hydrogenation using control methods having at least one of acetol (hydroxyacetone) and a tracer as inputs.

20 Claims, No Drawings

(56) References Cited

U.S. PATENT DOCUMENTS

| | | | |
|---|---|---|---|
| 10,138,184 | B2 | 11/2018 | Van Der Waal et al. |
| 10,221,116 | B2 | 3/2019 | Huizenga et al. |
| 10,233,138 | B2 | 3/2019 | Van Der Waal |
| 10,246,390 | B2 | 4/2019 | Huizenga et al. |
| 10,266,470 | B2 | 4/2019 | Huizenga et al. |
| 10,294,180 | B2 | 5/2019 | Van Der Waal et al. |
| 10,294,181 | B2 | 5/2019 | Chewter et al. |
| 10,308,577 | B2 | 6/2019 | Perez Golf et al. |
| 10,369,550 | B2 | 8/2019 | Edulji et al. |
| 10,450,249 | B2 | 10/2019 | Van Der Heide et al. |
| 10,450,255 | B2 | 10/2019 | Muthusamy |
| 10,464,870 | B2 | 11/2019 | Liu et al. |
| 10,478,809 | B2 | 11/2019 | Geyer et al. |
| 10,519,086 | B2 | 12/2019 | Muthusamy et al. |
| 10,556,226 | B2 | 2/2020 | Liu et al. |
| 10,562,012 | B2 | 2/2020 | Colijn et al. |
| 10,647,646 | B2 | 5/2020 | Van Der Heide |
| 10,647,647 | B2 | 5/2020 | Van Der Heide et al. |
| 10,654,782 | B2 | 5/2020 | Muthusamy et al. |
| 10,752,567 | B2 | 8/2020 | Muthusamy et al. |
| 11,008,269 | B2 | 5/2021 | Dekker et al. |
| 11,059,768 | B2 | 7/2021 | Van Der Waal et al. |
| 2011/0312487 | A1 | 12/2011 | Chen et al. |
| 2011/0312488 | A1 | 12/2011 | Chen et al. |
| 2014/0042358 | A1 | 2/2014 | Suppes |
| 2015/0329449 | A1 | 11/2015 | Schreck et al. |
| 2016/0207856 | A1 | 7/2016 | Van Der Heide et al. |
| 2016/0304423 | A1 | 10/2016 | Schreck et al. |
| 2017/0001932 | A1 | 1/2017 | Van der heide et al. |
| 2017/0210687 | A1 | 7/2017 | Liu et al. |
| 2017/0305823 | A1 | 10/2017 | Fischer et al. |
| 2017/0349513 | A1* | 12/2017 | Schreck ............ C07C 31/202 |
| 2018/0016214 | A1 | 1/2018 | Ma |
| 2018/0086681 | A1* | 3/2018 | Schreck ............ C07C 31/202 |
| 2018/0150037 | A1 | 5/2018 | Amrit et al. |
| 2018/0187219 | A1 | 7/2018 | Van Der Heide |
| 2018/0201559 | A1 | 7/2018 | Martin et al. |
| 2018/0272319 | A1 | 9/2018 | Muthusamy |
| 2018/0273452 | A1 | 9/2018 | Van Der Bijl et al. |
| 2018/0273453 | A1 | 9/2018 | Van Der Bijl et al. |
| 2018/0297920 | A1 | 10/2018 | Muthusamy et al. |
| 2018/0362424 | A1 | 12/2018 | Chewter et al. |
| 2018/0362425 | A1 | 12/2018 | Van Der Heide et al. |
| 2019/0010103 | A1 | 1/2019 | Osmundsen et al. |
| 2019/0010104 | A1 | 1/2019 | Holm et al. |
| 2019/0039979 | A1 | 2/2019 | Van Der Heide et al. |
| 2019/0047929 | A1 | 2/2019 | De Vlieger et al. |
| 2019/0084907 | A1 | 3/2019 | Huizenga et al. |
| 2019/0202764 | A1 | 7/2019 | Fischer et al. |
| 2019/0256446 | A1 | 8/2019 | Muthusamy et al. |
| 2019/0330417 | A1 | 10/2019 | Ren et al. |
| 2019/0359548 | A1 | 11/2019 | Liu et al. |
| 2020/0109098 | A1 | 4/2020 | Muthusamy |
| 2020/0325090 | A1 | 10/2020 | Fischer et al. |
| 2020/0377438 | A1 | 12/2020 | Huizenga et al. |
| 2020/0406237 | A1 | 12/2020 | Singh et al. |

FOREIGN PATENT DOCUMENTS

| | | |
|---|---|---|
| NL | 2014120 A | 9/2016 |
| WO | 2015154258 A1 | 10/2015 |
| WO | 2016001136 A1 | 1/2016 |
| WO | 2016114658 | 7/2016 |
| WO | 2016114659 A1 | 7/2016 |
| WO | 2016114660 A1 | 7/2016 |
| WO | 2016114661 A1 | 7/2016 |
| WO | 2016196752 A1 | 12/2016 |
| WO | 2017001382 A1 | 1/2017 |
| WO | 2017055285 A1 | 4/2017 |
| WO | 2017055289 A1 | 4/2017 |
| WO | 2017070067 | 4/2017 |
| WO | 2017085234 | 5/2017 |
| WO | 2017097839 A1 | 6/2017 |
| WO | 20170210687 A1 | 7/2017 |
| WO | 2017137355 A1 | 8/2017 |
| WO | 2017202731 A1 | 11/2017 |
| WO | WO 2018024787 A1 | 2/2018 |
| WO | 2018104508 A1 | 6/2018 |
| WO | 2020055796 A1 | 3/2020 |
| WO | 2020055831 A1 | 3/2020 |
| WO | 2020182456 A1 | 9/2020 |
| WO | 2020212542 A1 | 10/2020 |
| WO | 2021058805 A1 | 4/2021 |
| WO | 2021058808 A1 | 4/2021 |
| WO | 2021122853 A1 | 6/2021 |

OTHER PUBLICATIONS

Erik Lassner et al., "The Chemistry of Non-Sag Tungsten", 1995, pp. 111-117, Publisher: Pergamon.

Lekova, V.D et al., "Application of a ternary complex of tungsten(VI) with 4-nitrocatechol and thiazolyl blue for extraction-spectrophotometric determination of tungsten", "Chemical Papers", 2006, pp. 283-287, vol. 60, No. 4.

Makino et al., "Recovery and Recycling of Tungsten by Alkaline Leaching of Scrap and Charged Amino Group Assisted Precipitation", "ACS Sustainable Chem Eng", Jan. 19, 2018, pp. 4246-4252, vol. 6.

Mesbah et al., "Model Predictive Control of an Integrated Continuous Pharmaceutical Manufacturing Pilot Plant", "Organic Process Research and Development", May 17, 2017, pp. 844-854, vol. 21, No. 6, Publisher: ACS Publications.

Ogi et al., "Facile and Efficient Removal of Tungsten Anions Using Lysine-Promoted Precipitation for Recycling High-Purity Tungsten", "ACS Sustainable Chem Eng.", Feb. 18, 2017, pp. 3141-3147, vol. 5.

Jifeng Pang et al, "Catalytic conversion of cellulosic biomass to ethylene glycol: Effects of inorganic impurities in biomass", "Bioresource Technology", 2014, pp. 424-429, vol. 175, Publisher: Elsevier Ltd.

Pfrepper et al., "Continuous on-line chromatography of short lived isotopes of tungsten as homolog of seaborgium (element 106)", "RAdiochim Acta", Mar. 3, 200, pp. 273-278, vol. 88.

Sadighi-Bonabi et al., "Laser induced sonofusion: A new road toward thermonuclear reactions", "AIP Advances", Mar. 29, 2016, vol. 6, No. 3, Publisher: AIP Publishing.

Shen L. et al., "Thermodynamics of Tungsten Ores Decomposition Process Options", "The Minerals, Metals & Materials Series", 2018, Volume Extraction 2018.

Thanekar et al., "Application of Hydrodynamic Cavitation Reactors for Treatment of Wastewater Containing Organic Pollutants: Intensification Using Hybrid Approaches", "Fluids", Nov. 23, 2018, vol. 3, No. 98.

Wu et al., "Tungsten Recovery from Spent SCR Catalyst Using Alkaline Leaching and Ion Exchange", "Minerals", Oct. 17, 2016, vol. 6, No. 107.

Xi et al., "Production of Ethylene Glycol and Its Monether Derivative from Cellulose", "ACS Sustainable Chem. Eng.", Sep. 2, 2014, pp. 2355-262, vol. 2.

Zhang et al., "A Novel Process for Tungsten Hydrometallurgy Based on Direct Solvent Extraction in Alkaline Medium", "Hydrometallurgy", Jan. 1, 2016, pp. 233-237, vol. 165.

Zhao et al., "Ethylene Glycol Production from Glucose Over W—Ru Catalysts: Maximizing Yield by Kinetic Modeling and Simulation", Jun. 1, 2017, pp. 2072-2080, vol. 63, No. 6, Publisher: AlChE Journal.

Wikipedia, "Glucose", Jun. 13, 2019.

Wikipedia, "Hydroxyacetone", Aug. 19, 2018.

Yazdani et al., "Glucose hydrogenolysis over Cu-La2Oc/AlcO3: Mechanistic insights", "Molecular Catalysis", Jan. 1, 2019, pp. 138-145, vol. 466.

Matsuoka et al., "Retro=aldol-type fragmentation of reducing sugars preferntially occuriing in polyether at high temperature: Role of the ehter oxygen as a base catalyst", Journal of Analytical and Applied Pyrolysis, Jan. 1, 2012, pp. 24-32, vol. 93.

* cited by examiner

CONTINUOUS, CARBOHYDRATE TO ETHYLENE GLYCOL PROCESSES

CROSS-REFERENCE TO RELATED APPLICATION(S)

This application claims the benefit under 35 U.S.C. § 119(e) to U.S. Provisional Application 62/905,068, filed Sep. 24, 2019, and entitled METHODS FOR OPERATING CONTINUOUS, UNMODULATED, MULTIPLE CATALYTIC STEP PROCESSES, which is hereby incorporated herein by reference in its entirety for all purposes.

TECHNICAL FIELD

This invention pertains processes for the catalytic conversion of carbohydrate to ethylene glycol by the retro-aldol/hydrogenation route.

BACKGROUND

Ethylene glycol is a valuable commodity chemical that has a broad range of uses as both a building block for other materials such as polyethylene terephthalate (PET) and for its intrinsic properties such as for antifreeze. Ethylene glycol demand is substantial, making it one of the largest volume organic chemicals produced in the world. It is currently made by multistep processes which start with ethylene derived from hydrocarbon feedstocks.

Proposals have been made to manufacture ethylene glycol from renewable resources such as carbohydrates. These alternative processes include catalytic routes such as hydrogenolysis of sugar and a two-catalyst process using a retro-aldol catalyst to generate intermediates from sugar that can be hydrogenated over a hydrogenation catalyst to produce ethylene glycol and propylene glycol.

In the retro-aldol route, carbohydrate is converted over a retro-aldol catalyst to intermediates, and then the intermediates are then catalytically converted over a hydrogenation catalyst to ethylene glycol and/or propylene glycol in an unmodulated reaction zone. As used herein, the term unmodulated means that the process is conducted in a single pot or if in multiple vessels or regions, intermediates are not removed between vessels or zones. The sought initially-occurring retro-aldol reaction is endothermic and requires a high temperature, e.g., often over 230° C., to provide a sufficient reaction rate to preferentially favor the conversion of carbohydrate to intermediates. Under conditions that favor the retro-aldol conversion, isomerization of sugars can occur. For instance, aldose such as glucose, can be isomerized to fructose. Aldose, such as glucose, provide under retro-aldol conditions intermediates containing 2 carbon atoms such as glycol aldehyde that can be hydrogenated to ethylene glycol. Fructose, under retro-aldol conditions, is converted to, among other things, intermediates containing 3 carbon atoms that under hydrogenation conditions provide propylene glycol and glycerol. Additionally, retro-aldol intermediates such as glycol aldehyde can react to provide co-products such as 1,2-butanediol. Moreover, hydrogenation can result in degradation of ethylene glycol and propylene glycol. And since hydrogen is required, mass transfer of hydrogen to catalytic sites may be inadequate to support the hydrogenation, and this hydrogen starvation can result in co-products such as organic acids being produced. Accordingly, to optimize the production of ethylene glycol in an unmodulated reaction zone, the retro-aldol and hydrogenation conversion conditions need to be in balance.

A desire thus exists to provide methods for controlling retro-aldol/hydrogenation processes using an unmodulated reaction zone. Moreover, it is desired that such methods use input parameters that can be reasonably obtained from the process, especially input parameters that can be ascertained relatively quickly to provide real-time data regarding the operation of the process.

BRIEF SUMMARY

By this invention processes are provided for the conversion of carbohydrate to ethylene glycol by retro-aldol catalysis and sequential hydrogenation using control methods having at least one of acetol (hydroxyacetone) and at least one tracer as inputs. A tracer precursor is one or more ketones of 3 to 6, preferably 4 to 6, carbons and the tracer is one or more of unreacted tracer precursor and hydrogenation products of the ketone such as alcohols in the raw product resulting from the supply of the ketone to the reaction zone. Acetol concentration in raw product reflects both information about the relative amount of aldose isomerization as it is a three-carbon compound derived from the retro-aldol catalysis of fructose and the hydrogenation. A carbonyl of a ketone does not undergo retro-aldol conversion, and thus the tracer reflects on hydrogenation strength. Since the conversion of carbohydrate does not result in the coproduction of hydrocarbons only having internal carbonyls or internal hydroxyls, the input based upon one or more tracers is not confounded as a coproduct. The control systems useful for the retro-aldol/hydrogenation conversion of carbohydrate to ethylene glycol will employ a number of other inputs such as one or more of pressure, temperature, residence time, pH, raw product composition, feed compositions and rates, and the like. Acetol and/or tracer provide information not otherwise readily available about the condition of the process, and thus their use as inputs to a control system can provide a more robust and useful control of the process. Increases in acetol concentration in the raw product have been found by this invention to presage an observable decrease in selectivity to ethylene glycol. Hence, process changes can be implemented timely to maintain conversion and selectivity to ethylene glycol. Similarly, the tracer specifically targets hydrogenation activity and facilitates unconfounding whether a change in a by-product or product production is due to issues with the retro-aldol catalytic activity or hydrogenation catalytic activity.

Any suitable process control system can be used, and more expansive control systems for the process which systems can be design space systems (DSC) or model predictive control systems (MPC), both of which are well known in the art, are often preferred. In a DSC, boundary conditions, or windows, are predetermined and operation within the windows is considered to be under control. In an MPC, dynamic process models, which are often empirically generated, take into account current control status as well as its effect on the process in the future. Control actions in an MPC can be taken based upon the predictive models in anticipation of future events. However, the disclosed processes which use either or both of acetol and tracer in the raw product, enhance the ability to control the process regardless of whether the control is manual or based on sophisticated control systems.

One broad aspect pertains to a continuous processes having a control system to control one or more operating parameters based on one or more inputs for the catalytic conversion of a carbohydrate feed containing at least aldose-yielding or ketose-yielding carbohydrate to lower glycol of at least one of ethylene glycol and propylene glycol in an unmodulated reaction zone by sequential retro-aldol catalytic conversion under retro-aldol conditions, including the presence of a retro-aldol catalyst providing retro-aldol catalytic activity in liquid medium in the unmodulated reaction zone, to intermediates and catalytic hydrogenation of intermediates under hydrogenation conditions, including the presence of hydrogen and hydrogenation catalyst providing hydrogenation catalytic activity, to lower glycol, in the unmodulated reaction zone, and withdrawing continuously or intermittently from said unmodulated reaction zone, a raw product, said process comprising controlling at least one operating parameter of the process using at least the concentration of acetol in the raw product is an input to the control system for the process. Preferably the carbohydrate comprises aldose and the lower glycol comprises ethylene glycol.

Acetol is derived from fructose, and thus its concentration is dependent upon the fructose generated, and thus changes in the concentration of fructose need to be taken into account. In preferred processes for making ethylene glycol, in response to an increase in acetol concentration without evidence of a reduction in retro-aldol catalytic activity, at least one of (i) the hydrogenation catalytic activity is increased and (ii) at least one of the rate of supply of the carbohydrate feed and the concentration of the carbohydrate in the feed, is decreased. Where evidence of a reduction in retro-aldol catalytic activity exists, for instance, with an increase in mannitol or glycerol, an increase in acetol, if greater than expected from the reduction in retro-aldol catalytic activity, would indicate that at least one of the rate of supply of the carbohydrate feed and the concentration of the carbohydrate in the feed, is decreased until the retro-aldol catalytic activity is reestablished.

Another broad aspect pertains to continuous processes having a control system to control one or more operating parameters based on input for the catalytic conversion of a carbohydrate feed containing at least aldose-yielding or ketose-yielding carbohydrate to lower glycol of at least one of ethylene glycol and propylene glycol in an unmodulated reaction zone by sequential retro-aldol catalytic conversion under retro-aldol conditions, including the presence of a retro-aldol catalyst providing retro-aldol catalytic activity in a liquid medium in the unmodulated reaction zone, to intermediates and catalytic hydrogenation of intermediates under hydrogenation conditions, including the presence of hydrogen and hydrogenation catalyst providing hydrogenation catalytic activity, to lower glycol, in the unmodulated reaction zone, supplying a ketone of 3 to 6, preferably 4 to 6, carbons to the reaction zone from which a tracer is produced under conditions in the reaction zone and withdrawing continuously or intermittently from said unmodulated reaction zone, a raw product, said process comprising controlling at least one operating parameter of the process using at least the concentration of at least one component of the tracer in the raw product is an input value to the control system for the process.

Where the tracer indicates a change in the hydrogenation of the ketone, preferably the at least one of (i) the absolute amounts of catalytically active species and relative amounts of each of the retro-aldol catalytic activity and hydrogenation catalytic activity, and (ii) at least one of the rate of feed, and carbohydrate concentration, to the reaction zone are adjusted. Where more ketone is hydrogenated, often at least the rate of feed to the reaction zone is increased or the hydrogenation catalytic activity is decreased. Where less ketone is hydrogenated, preferably either or both of (i) the hydrogenation catalyst activity in the reaction zone is increased and (ii) at least one of the rate of feed and the concentration of carbohydrate to the reaction zone is decreased.

In many instances, the retro-aldol catalyst is homogeneous and the hydrogenation catalyst is heterogeneous. The desired process objective is often the selectivity of conversion to ethylene glycol, and in some instances, the selectivity to the total of ethylene glycol and propylene glycol ("total lower glycol") is greater than about 75 mass percent based upon the mass of the feed. In some instances, the concentrations of acetol or at least one component of the tracer can be compared with concentrations of at least one of itol, 1,2-butanediol, pH and, in the case of acetol, tracer if used, and in the case of tracer being used, acetol, in the raw product for purposes of process control. The reaction process can be a cascade process or a single pot process. When making ethylene glycol, acetol concentrations are often compared to concentrations of at least one of sorbitol, 1.2-butanediol and glycerol. When making ethylene glycol, tracer concentrations are often compared with concentrations of at least one of sorbitol and glycerol.

The use of a tracer precursor can be continuous or intermittent. For instance, the tracer precursor can be used intermittently to assure that the process is performing as desired or to assist in troubleshooting a problem in the operation of the process and to bring the process back into alignment with desired operation. The disclosed processes can also be used, e.g., in laboratory or pilot scale operations, to evaluate hydrogenation catalysts and hydrogenation catalytic activity for research, development or qualification purposes, or can be used to evaluate ex-situ samples of catalyst and hydrogenation catalytic activity being used or to be used in a larger, e.g., commercial-scale process. The ex-situ evaluations can be used as a parameter for use in the control system for the process.

While multiple embodiments are disclosed, still other embodiments of the disclosure will become apparent to those skilled in the art from the following detailed description, which shows and describes illustrative embodiments of the invention. As will be realized, the disclosure is capable of modifications in various obvious aspects, all without departing from the spirit and scope of the disclosure. Accordingly, the drawings and detailed description are to be regarded as illustrative in nature and not restrictive.

DETAILED DESCRIPTION

All patents, published patent applications and articles referenced herein are hereby incorporated by reference in their entirety.

Definitions

As used herein, the following terms have the meanings set forth below unless otherwise stated or clear from the context of their use.

Where ranges are used herein, the end points only of the ranges are stated so as to avoid having to set out at length and describe each and every value included in the range. Any appropriate intermediate value and range between the recited endpoints can be selected. By way of example, if a range of between 0.1 and 1.0 is recited, all intermediate values (e.g., 0.2, 0.3, 0.63, 0.815 and so forth) are included as are all intermediate ranges (e.g., 0.2-0.5, 0.54-0.913, and so forth).

The use of the terms "a" and "an" is intended to include one or more of the element described.

Admixing or admixed means the formation of a physical combination of two or more elements which may have a uniform or non-uniform composition throughout and includes, but is not limited to, solid mixtures, solutions and suspensions.

Bio-sourced carbohydrate feedstock means a product that includes carbohydrates sourced, derived or synthesized from, in whole or in significant part, to biological products or renewable agricultural materials (including, but not limited to, plant, animal and marine materials) or forestry materials.

By-products are incidental or secondary products made in the manufacture of the sought product and include the incidental or secondary products and intermediates to these products and include reaction products from the sought product. By-products do not include intermediates to the sought product. By way of example, in the catalytic conversion of glucose to ethylene glycol, any unreacted glycol aldehyde would not be a by-product but hydroxyacetone would be a byproduct, even though either might be able to be further reacted under the conditions of the reaction. Other by-products include, but are not limited to, mannitol, sorbitol, glycerol, 1,2-butanediol, erythritol, threitol, organic acids, and gases.

Catalyst means a heterogeneous or homogeneous catalyst. For purposes herein, catalysts that behave as if they are dissolved in the media, e.g., a colloidal suspension, are considered to be homogeneous catalysts regardless of whether or not they are dissolved. A catalyst can contain one or more catalytic metals, and for heterogeneous catalysts, include supports, binders and other adjuvants. Catalytic metals are metals that are in their elemental state or are ionic or covalently bonded. The term catalytic metals refers to metals that are not necessarily in a catalytically active state, but when not in a catalytically active state, have the potential to become catalytically active. Catalytic metals can provide catalytic activity or modify catalytic activity such as promotors, selectivity modifiers, and the like.

Catalytic activity or performance refers to the extrinsic activity of a catalyst in the reaction zone. Thus, the factors that affect catalyst activity include the condition of the catalyst per se, but also include its deployment in the reaction zone. For example, if a portion of the catalyst is physically occluded in the reaction zone, it is relatively unavailable for effecting the sought catalytic conversion even though it may be active per se. Mixing or other means of redistribution to make the catalyst surface accessible would thus improve the extrinsic catalytic activity.

A change in catalytic activity can result from a change in the catalyst per se such as a chemical change, physical degradation, redistribution of components on the catalyst, loss of catalytically-active species from the catalyst, or poisoning or other effect from a component that become deposited or reacted during the course of the reaction. A change in catalytic activity can also be caused by the environment around the catalyst where the catalyst itself may be relatively unchanged, e.g., through steric effects or reactions or complexing with the components to be catalytically converted. Therefore, an increase or decrease in catalytic activity can, but does not necessarily, result from an increase or decrease in the mass of catalyst per unit volume.

Commencing contact means that a fluid starts a contact with a component, e.g., a medium containing a homogeneous or heterogeneous catalyst, but does not require that all molecules of that fluid contact the catalyst.

Conversion efficiency is the mass percent of a raw material that is converted in the process to chemical product.

Hydraulic distribution means the distribution of an aqueous solution in a vessel including contact with any catalyst contained therein.

Intermediate means a compound that can be further reacted under the conditions in the reaction zone to the sought product. As defined herein, an intermediate to a by-product is itself deemed to be a by-product.

Intermittently means from time to time and may be at regular or irregular time intervals.

Input values mean input information from the process for the control method. The inputs can be manipulative inputs, sometimes referred to as independent variables, which means that the value being reported is subject to control such as temperature. The inputs can be process parameters, sometimes referred to as dependent variables, which means that the determined value is resulting from multiple manipulative variables in the process. For instance, concentration of an intermediate, by-product or chemical product is the result of the combined set of process conditions. An input value can be from one or two or more manipulative inputs and process parameter inputs and can require calculations. For example, conversion efficiency can be determined from raw material concentration in the feed and the feed rate to the reaction zone and from the concentration of the chemical product in the effluent from the reaction zone and the flow rate of the effluent.

Itols are polyhydric alcohols with each carbon having a hydroxyl group, e.g., sugar alcohols.

Liquid medium means the liquid in the reactor. The liquid is a solvent for the carbohydrate, intermediates and products and for the homogeneous, tungsten-containing retro-aldol catalyst. Typically and preferably, the liquid contains at least some water and is thus termed an aqueous medium.

Operating parameters, or process parameters for the process are controllable parameters including, but not limited to temperature, pressure, feed rates and concentrations of reactants, residence time, adjuvants, pH, and hydrogenation catalytic activity and retro-aldol catalytic activity.

Organics capable of being hydrogenated ("HOC's") are oxygen-containing hydrocarbons capable of being hydrogenated under process conditions to one or more products. HOC's include, but are not limited to, sugars and other ketones and aldehydes and hydroxyl-containing hydrocarbons such as alcohols, diols and itols.

The pH of an aqueous solution is determined at ambient pressure and temperature. In determining the pH of, for example the aqueous, hydrogenation medium or the product solution, the liquid is cooled and allowed to reside at ambient pressure and temperature for 2 hours before determination of the pH. Where the solution for which the pH measurement is sought contains less than about 50 mass percent water, water is added to the solution to provide greater than 50 mass percent water. For purposes of consistency, the dilution of solutions is to the same mass percent water.

pH control agents mean one or more of buffers and acids or bases.

The term raw material is used to indicate one or more reactant that are added to the reaction zone in the process and is not intended to reflect on purity or need for refining. The raw material can be a product from another chemical or biochemical process. Since reactants include intermediates, the term raw material thus facilitates understanding.

A reaction zone is the volume that contains the first and second catalyst and can be a single vessel or plural vessels, or reactors.

A reactor can be one or more vessels in series or in parallel and a vessel can contain one or more zones. A reactor can be of any suitable design for continuous operation including, but not limited to, tanks and pipe or tubular reactors and can have, if desired, fluid mixing capabilities. Types of reactors include, but are not limited to, laminar flow reactors, fixed bed reactors, slurry reactors, fluidized bed reactors, moving bed reactors, simulated moving bed reactors, trickle-bed reactors, bubble column and loop reactors.

Discussion

The processes for the conversion of carbohydrate that contains an aldohexose-yielding carbohydrate or ketose-yielding carbohydrate to at least one of ethylene glycol and propylene glycol (lower glycol) in a reaction zone are effected by subjecting the sugar to catalytic retro-aldol conditions to produce intermediate that is hydrogenated under catalytic hydrogenation conditions. See, for instance, U.S. published patent applications 2017/0349513 and 2018/0086681 and U.S. Pat. Nos. 9,399,610 and 9,783,472, all hereby incorporated by reference in their entireties.

The raw material comprises carbohydrate which is most often at least one of pentose and hexose or compounds that yield pentose or hexose. Examples of pentose and hexose include xylose, lyxose, ribose, arabinose, xylulose, ribulose, glucose, mannose, galactose, allose, altrose, idose, talose, and gulose fructose, psicose, sorbose, and tagatose. Most bio-sourced carbohydrate feedstocks yield glucose upon being hydrolyzed. Glucose precursors include, but are not limited to, maltose, trehalose, cellobiose, kojibiose, nigerose, nigerose, isomaltose, β,β-trehalose, α,β-trehalose, sophorose, laminaribiose, gentiobiose, and mannobiose. Carbohydrate polymers and oligomers such as hemicellulose, partially hydrolyzed forms of hemicellulose, disaccharides such as sucrose, lactulose, lactose, turanose, maltulose, palatinose, gentiobiulose, melibiose, and melibiulose, or combinations thereof may be used.

The carbohydrate feed can be solid or, preferably, in a liquid suspension or dissolved in a solvent such as water. Where the carbohydrate feed is in a non-aqueous environment, it is preferred that the carbohydrate is at least partially hydrated. Non-aqueous solvents include alkanols, diols and polyols, ethers, or other suitable carbon compounds of 1 to 6 carbon atoms. Solvents include mixed solvents, especially mixed solvents containing water and one of the aforementioned non-aqueous solvents. Certain mixed solvents can have higher concentrations of dissolved hydrogen under the conditions of the hydrogenation reaction and thus reduce the potential for hydrogen starvation. Preferred non-aqueous solvents are those that can be hydrogen donors such as isopropanol. Often these hydrogen donor solvents have the hydroxyl group converted to a carbonyl when donating a hydrogen atom, which carbonyl can be reduced under the conditions in the reaction zone. Most preferably, the carbohydrate feed is provided in an aqueous solution. In any event, the volume of feed and the volume of raw product withdrawn need to balance to provide for a continuous process.

Further considerations in providing the carbohydrate to the reaction zone are minimizing energy and capital costs. For instance, in steady state operation, the solvent contained in the feed exits the reaction zone with the raw products and needs to be separated in order to recover the sought glycol products.

Preferably, the feed is introduced into the reaction zone in a manner such undue concentrations of HOC's that can result in hydrogen starvation are avoided. With the use of a greater number of multiple locations for the supply of carbohydrate per unit volume of the reaction zone, the more concentrated the carbohydrate in the feed can be. In general, the mass ratio of water to carbohydrate in the carbohydrate feed is preferably in the range of 4:1 to 1:4. Aqueous solutions of 600 or more grams per liter of certain carbohydrates such as dextrose and sucrose are sometimes commercially available.

The carbohydrate contained in the carbohydrate feed is provided at a rate of at least 50 or 100, and preferably, from about 150 to 500 grams per liter of reactor volume per hour. Optionally, a separate reaction zone can be used that contains retro-aldol catalyst with an essential absence of hydrogenation catalyst.

In these processes, an liquid medium containing the carbohydrate is contacted with retro-aldol catalyst under retro-aldol reaction conditions. The contact may commence prior to or upon introducing the liquid medium into a hydrogenation catalyst-containing portion of the reaction zone. The preferred temperatures for retro-aldol reactions are typically from about 230° C. to 300° C., and more preferably from about 240° C. to 280° C., although retro-aldol reactions can occur at lower temperatures, e.g., as low as 90° C. or 150° C. The pressures (absolute) are typically in the range of about 15 to 200 bar (1500 to 20,000 kPa), say, from about 25 to 150 bar (2500 and 15000 kPa).

Retro-aldol reaction conditions include the presence of retro-aldol catalyst. A retro-aldol catalyst is a catalyst that catalyzes the retro-aldol reaction. Examples of compounds that can provide retro-aldol catalyst include, but are not limited to, heterogeneous and homogeneous catalysts, including catalyst supported on a carrier, comprising tungsten and its oxides, sulfates, phosphides, nitrides, carbides, halides, acids and the like. Tungsten carbide, soluble phosphotungstens, tungsten oxides supported on zirconia, alumina and alumina-silica are also included. Preferred catalysts are provided by soluble tungsten compounds and mixtures of tungsten compounds. Soluble tungstates include, but are not limited to, ammonium and alkali metal, e.g., sodium and potassium, paratungstate, partially neutralized tungstic acid, ammonium and alkali metal metatungstate and ammonium and alkali metal tungstate. Often the presence of ammonium cation results in the generation of amine by-products that are undesirable in the lower glycol product. Without wishing to be limited to theory, the species that exhibit the catalytic activity may or may not be the same as the soluble tungsten compounds introduced as a catalyst. Rather, a catalytically active species may be formed as a result of exposure to the retro-aldol reaction conditions. Tungsten-containing complexes are typically pH dependent. For instance, a solution containing sodium tungstate at a pH greater than 7 will generate sodium metatungstate when the pH is lowered. The form of the complexed tungstate anions is generally pH dependent. The rate that complexed anions formed from the condensation of tungstate anions are formed is influenced by the concentration of tungsten-containing anions. A preferred retro-aldol catalyst comprises ammonium or alkali metal tungstate that becomes partially neutralized with acid, preferably an organic acid of 1 to 6 carbons such as, but without limitation, formic acid, acetic acid, glycolic acid, and lactic acid. The partial neutralization is often from about 25 to 75%, i.e., on average from 25 to 75% of the cations of the tungstate become acid sites. The partial neutralization may occur prior to introducing the tungsten-containing compound into the reactor or with acid contained in the reactor.

The concentration of retro-aldol catalyst used may vary widely and will depend upon the activity of the catalyst and the other conditions of the retro-aldol reaction such as acidity, temperature and concentrations of carbohydrate. Typically, the retro-aldol catalyst is provided in an amount to provide from about 0.01 or 0.05 to 100, say, from about 0.02 or 0.1 to 50, grams of tungsten calculated as the elemental metal per liter of aqueous, hydrogenation medium. The retro-aldol catalyst can be added as a mixture with all or a portion of the carbohydrate feed or as a separate feed to the aqueous, hydrogenation medium or with recycling liquid medium or any combination thereof. In some instances, a homogeneous, tungsten-containing retro-aldol catalyst can deposit a tungsten-containing compound or complex on the hydrogenation catalyst and adversely affect the activity of the hydrogenation catalyst. A continuous or intermittent cycling of the amount of tungsten-containing catalyst can result in removal of at least a portion of the deposited tungsten compound or complex. The disclosed methods thus contemplate that the control of the absolute amount of catalytically active species and relative amounts of each of the first catalyst and second catalyst includes operations where the process objective is a rejuvenation of a catalyst. The disclosed methods also contemplate that the control of the absolute amount of catalytically active species and relative amounts of each of the first catalyst and second catalyst includes operations where the process objective is a reduction of the catalytic activity of one of the first or second catalysts. The reduction in the catalytic activity can be achieved by any suitable means, including, but not limited to, one or more of reducing the concentration of the catalyst in the liquid medium, selective poisoning of catalytically active species of the catalyst, and providing additives or modifiers that reduce catalytic activity without necessarily reducing catalytically active species.

Frequently the carbohydrate feed is subjected to retro-aldol conditions prior to being introduced into the aqueous, hydrogenation medium in the reaction zone containing hydrogenation catalyst. Preferably the introduction into the aqueous, hydrogenation medium occurs in less than one minute, and most often less than 10 seconds, from the commencement of subjecting the carbohydrate feed to the retro-aldol conditions. Some, or all of the retro-aldol reaction can occur in the reaction zone containing the hydrogenation catalyst. In any event, the most preferred processes where isomerization of glucose to fructose is undesirable, are those having a short duration of time between the retro-aldol conversion and hydrogenation.

The hydrogenation, that is, the addition of hydrogen atoms to an organic compound without cleaving carbon-to-carbon bonds, can be conducted at a temperature in the range of about 100° C. or 120° C. to 300° C. or more. Typically, the aqueous, hydrogenation medium is maintained at a temperature of at least about 230° C. until substantially all carbohydrate is reacted to have the carbohydrate carbon-carbon bonds broken by the retro-aldol reaction, thereby enhancing selectivity to ethylene and propylene glycol. Thereafter, if desired, the temperature of the aqueous, hydrogenation medium can be reduced. However, the hydrogenation proceeds rapidly at these higher temperatures. Thus, the temperatures for hydrogenation reactions are frequently from about 230° C. to 300° C., say, from 240° C. to 280° C. The pressures are typically in the range of about 15 to 200 bar, say, from about 25 to 150 bar. The hydrogenation reactions require the presence of hydrogen as well as hydrogenation catalyst. Hydrogen has low solubility in aqueous solutions. The concentration of hydrogen in the aqueous, hydrogenation medium is increased with increased partial pressure of hydrogen in the reaction zone. The pH of the aqueous, hydrogenation medium is often at least about 3, say, from about 3 or 3.5 to 8, and in some instances from about 3.2 or 4 to 7.5.

The hydrogenation is conducted in the presence of a hydrogenation catalyst. Frequently the hydrogenation catalyst is a heterogeneous catalyst. It can be deployed in any suitable manner, including, but not limited to, fixed bed, fluidized bed, trickle bed, moving bed, slurry bed, and structured bed. Nickel, ruthenium, palladium and platinum are among the more widely used reducing metal catalysts. However, many reducing catalysts will work in this application. The reducing catalyst can be chosen from a wide variety of supported transition metal catalysts. Nickel, Pt, Pd and ruthenium as the primary reducing metal components are well known for their ability to reduce carbonyls. One particularly favored catalyst for the reducing catalyst in this process is a supported, Ni—Re catalyst. A similar version of Ni/Re or Ni/Ir can be used with good selectivity for the conversion of the formed glycolaldehyde to ethylene glycol. Nickel-rhenium is a preferred reducing metal catalyst and may be supported on alumina, alumina-silica, silica or other supports. Supported Ni—Re catalysts with B as a promoter are useful. Generally, for slurry reactors, a supported hydrogenation catalyst is provided in an amount of less than 10, and sometimes less than about 5, say, about 0.1 or 0.5 to 3, grams per liter of nickel (calculated as elemental nickel) per liter of liquid medium in the reactor. As stated above, not all the nickel in the catalyst is in the zero-valence state, nor is all the nickel in the zero-valence state readily accessible by glycol aldehyde or hydrogen. Hence, for a particular hydrogenation catalyst, the optimal mass of nickel per liter of liquid medium will vary. For instance, Raney nickel catalysts would provide a much greater concentration of nickel per liter of liquid medium. Frequently in a slurry reactor, the hydrogenation catalyst is provided in an amount of at least about 5 or 10, and more often, from about 10 to 70 or 100, grams per liter of aqueous, hydrogenation medium and in a packed bed reactor the hydrogenation catalyst comprises about 20 to 80 volume percent of the reactor. In some instances, the weight hourly space velocity is from about 0.01 or 0.05 to 1 $hr^{-1}$ based upon total carbohydrate in the feed. Preferably the residence time is sufficient that glycol aldehyde and glucose are less than 0.1 mass percent of the reaction product, and most preferably are less than 0.001 mass percent of the reaction product.

In the disclosed processes, the combination of reaction conditions (e.g., temperature, hydrogen partial pressure, concentration of catalysts, hydraulic distribution, and residence time) are sufficient to convert at least about 95, often at least about 98, mass percent and sometimes essentially all of the carbohydrate that yield aldose or ketose. It is well within the skill of the artisan having the benefit of the disclosure herein to determine the set or sets of conditions that will provide the sought conversion of the carbohydrate.

Optimizing the retro-aldol process to make ethylene glycol involves optimizing the retro-aldol conversion, which is primarily kinetic limited, and the hydrogenation reaction which is primarily mass transfer limited. Mass transfer limitations include the supply of hydrogen to the hydrogenation catalytic sites, and hydrogen starvation can occur where localized regions of high hydrogenation catalytic active exist. The hydrogen starvation can be caused by, by way of example and not in limitation, maldistribution of the hydrogenation catalyst within the reaction zone and localized regions of higher feed concentration in the reaction zone. Hydrogen starvation thus can result in the formation of organic acids, and organic acids can be a by-product in the withdrawn medium. For purposes of process control, pH determinations can often be used as a proxy for organic acid concentration. In some instances, reducing the rate of feed can attenuate the generation of acids; however, manipulation of one or both of the absolute amount and relative amounts of retro-aldol catalyst and hydrogenation catalyst may also be required.

The acetol or tracer is often used in connection with other parameter observations. Especially with acetol, which presages observable reductions in conversion and selectivity to ethylene glycol, a change can be used to trigger reviewing changes in other parameters to ascertain process changes to be made to prevent a significant disruption of the process, and preferably, avoid material losses of conversion and selectivity to ethylene glycol. In one embodiment, an increase in acetol triggers the addition of a tracer precursor to evaluate catalytic hydrogenation activity or triggers a removal of a portion of the hydrogenation catalyst for an ex-situ evaluation.

Frequently, an additional process parameter input for process control is the concentration in the withdrawn medium of at least one of itol and 1,2-butanediol. The itols contained in the withdrawn medium result from reactions with the carbohydrate feed. Glucose, for instance, can be hydrogenated to sorbitol. In the retro-aldol step, glucose can provide glycol aldehyde and erythrose and, if isomerized, threose. These four carbon sugars, when hydrogenated, produce erythritol and threitol. Glucose can also undergo isomerization to fructose, and fructose, when hydrogenated, go to mannitol and sorbitol. Also, fructose under retro-aldol conditions, goes to three carbon compounds and thus glycerol can be produced. Because of the genesis of the itols, insights into the process can be obtained from the type and the rate of production of the itols.

As a general matter, an increase in itol concentration, all other things remaining substantially constant, is indicative that the retro-aldol catalytic activity has suffered, and one example of a manipulative inputs would be an adjustment to at least one of (I) the absolute amount and relative amounts of each of the retro-aldol catalytic activity and hydrogenation catalytic by increasing the retro-aldol catalytic activity or decreasing the hydrogenation catalytic activity, and (II) reducing the rate of feed of the raw material to the reaction zone.

If 1,2-butanediol concentration is used as a process parameter input, the 1,2-butanediol can result from the reaction between two glycolaldehyde molecules or from the dehydration of a tetrose. In the former, the general rule is that an increase in the 1,2-butanediol concentration is reflecting a loss of hydrogenation catalyst activity in the reaction zone, all other things remaining substantially the same. In this case, an example of an adjustment of manipulative inputs would be to at least one of (I) the absolute amount and relative amounts of each of the retro-aldol catalyst and hydrogenation catalyst by increasing the catalyst activity of the hydrogenation catalyst or decreasing the catalyst activity of the retro-aldol catalyst, and (II) reducing the rate of feed of the raw material to the reaction zone. In the latter, the retro-aldol conversion activity is likely inadequate, and (I) increasing activity of the retro-aldol catalyst, and (II) at least one of reducing the rate of feed of the raw material and its concentration to the reaction zone, would be responsive actions. Thus, having another parameter to directionally indicate whether the change in concentration of 1,2-butanediol can be helpful. For example, if an increase in 1,2-butandiol is accompanied by an increase in glycerol, which is made from fructose, which is from the isomerization of glucose, would be indicative of a reduction in retro-aldol activity since the isomerization reaction is out pacing the retro-aldol conversions, all else remaining the same.

Acetol is usually present in the withdrawn medium in a very low concentration. It has been found, however, that an increase of acetol is a sensitive indicator of a decrease in activity of the hydrogenation catalyst, especially where the concentration of fructose has not substantially changed. An increase in acetol concentration, under these circumstances can be addressed by increasing the catalytic activity of the hydrogenation catalyst and/or reducing the rate of raw material feed or its concentration to the reaction zone. In some instances, the acetol concentration in the withdrawn medium is less than 0.15 mass percent, preferably less than 0.10 mass percent.

A tracer can be used similarly to acetol. Ketones such as methyl ethyl ketone are useful to provide tracers for the retro-aldol/hydrogenation process as the internal carbonyl is more resistant to hydrogenation than the carbonyl of an aldehyde. The extent of hydrogenation of the ketone is thus an indicator of the hydrogenation activity in the reaction zone. The concentration of the ketone can vary widely and will depend upon, for instance, the ability to analytically detect the concentration of a tracer in the withdrawn medium. Often the concentration of the tracer is in the range of between about 1 part per million to 1 percent, by mass based upon mass of the medium.

The control system and control system hardware used is not critical to the broad processes of this invention, and any suitable control system, including manual, can be used. Design space and model predictive control are well known and are multivariate and are preferred. The former is based upon models and manipulative inputs values are maintained to windows of acceptable operation. Where manipulative inputs are interrelated, the design space control systems can be designed with predictive models such that adjustments in one manipulative input coincide with adjustments in one or more other manipulative inputs. The later considers not only the instantaneous state of the process but also the future state of the process. The models can be developed on, for instance, a linear or quadratic models. These models can be derived from empirical data and the performance of the process with respect to process objectives. With respect to model predictive control, data from the process can be used to refine the future predictive aspect of the models. The control systems can be open loop or closed loop, and where closed loop, the loop can be the entire plant or a portion thereof.

Although the disclosure has been described with references to various embodiments, persons skilled in the art will recognized that changes may be made in form and detail without departing from the spirit and scope of this disclosure.

What is claimed is:

1. A continuous process having a control system to control one or more operating parameters based on one or more inputs for the catalytic conversion of a carbohydrate feed containing at least aldose-yielding or ketose-yielding carbohydrate to lower glycol of at least one of ethylene glycol and propylene glycol in an unmodulated reaction zone by sequential retro-aldol catalytic conversion under retro-aldol conditions, including the presence of a retro-aldol catalyst providing retro-aldol catalytic activity in a liquid medium in the unmodulated reaction zone, to intermediates and catalytic hydrogenation of intermediates under hydrogenation conditions, including the presence of hydrogen and hydrogenation catalyst providing hydrogenation catalytic activity, to lower glycol, in the unmodulated reaction zone, and withdrawing continuously or intermittently from said unmodulated reaction zone, a raw product, said process comprising controlling at least one operating parameter of the process using at least the concentration of acetol in the raw product is an input to the control system for the process.

2. The process of claim 1 wherein the carbohydrate comprises aldose and the lower glycol comprises ethylene glycol.

3. The process of claim 2 wherein in response to an increase in acetol concentration, at least one of (i) the hydrogenation catalytic activity is increased and (ii) at least one of the rate of supply of the carbohydrate feed and the concentration of carbohydrate in the feed is decreased.

4. The process of claim 2 wherein the retro-aldol catalyst is homogeneous and the hydrogenation catalyst is heterogeneous.

5. The process of claim 2 wherein the concentration of acetol is compared with concentrations of at least one of itol, 1,2-butanediol, and pH in the raw product for purposes of process control.

6. The process of claim 5 wherein in response to an increase in acetol concentration and an increase in the concentration of at least one of sorbitol, 1,2-butanediol, and glycerol in the raw product, the retro-aldol catalytic activity is increased.

7. The process of claim 2 wherein the hydroxyacetone concentration is maintained less than about 0.15 mass percent of the raw product.

8. The process of claim 2 wherein in response to an increase in acetol accompanied by an increase in at least one of mannitol and glycerol, at least one of the rate of supply of the carbohydrate feed and the concentration of the carbohydrate in the feed, is decreased until retro-aldol catalytic activity is increased.

9. The process of claim 1 wherein the reaction zone is a cascade reaction zone.

10. A continuous process having a control system to control one or more operating parameters based on input for the catalytic conversion of a carbohydrate feed containing at least aldose-yielding or ketose-yielding carbohydrate to lower glycol of at least one of ethylene glycol and propylene glycol in an unmodulated reaction zone by sequential retro-aldol catalytic conversion under retro-aldol conditions, including the presence of a retro-aldol catalyst providing retro-aldol catalytic activity in a liquid medium in the unmodulated reaction zone, to intermediates and catalytic hydrogenation of intermediates under hydrogenation conditions, including the presence of hydrogen and hydrogenation catalyst providing hydrogenation catalytic activity, to lower glycol, in the unmodulated reaction zone, supplying a tracer precursor comprising a ketone of 3 to 6 carbons to the reaction zone from which at least one tracer is produced under conditions in the reaction zone and withdrawing continuously or intermittently from said unmodulated reaction zone, a raw product, said process comprising controlling at least one operating parameter of the process using at least the concentration of at least one component of the tracer in the raw product is an input to the control system for the process.

11. The process of claim 10 wherein where the tracer in the raw product indicates a change in the portion of the tracer precursor hydrogenated, then at least one of (i) the absolute amounts of catalytically active species and relative amounts of each of the retro-aldol catalytic activity and hydrogenation catalytic activity, and (ii) at least one of the rate of feed and concentration of carbohydrate in the feed to the reaction zone are adjusted.

12. The process of claim 11 where the concentration of a tracer in the raw product indicates that a greater portion of the tracer precursor is hydrogenated, either or both the rate of feed to the reaction zone is increased or the hydrogenation catalyst activity in the reaction zone is decreased.

13. The process of claim 11 where the concentration of a tracer in the raw product indicates that a lesser portion of the tracer precursor is hydrogenated, either or both of (i) the hydrogenation catalyst activity in the reaction zone is increased and (ii) at least one of the rate of feed and the concentration of carbohydrate in the feed to the reaction zone is decreased.

14. The process of claim 10 wherein the retro-aldol catalyst is homogeneous and the hydrogenation catalyst is heterogeneous.

15. The process of claim 10 wherein the carbohydrate comprises aldose and the lower glycol comprises ethylene glycol, concentrations of at least one component of the tracer is compared with concentrations of at least one of itol, 1,2-butanediol, acetol and pH in the raw product for purposes of process control.

16. The process of claim 15 where the tracer in the raw product indicates a substantially constant in the portion of the tracer precursor being hydrogenated and an increase in the concentration of at least one of sorbitol and glycerol in the raw product, the retro-aldol catalytic activity is increased.

17. The process of claim 15 where the tracer in the raw product indicates a decrease in the portion of the tracer precursor being hydrogenated and no increase in the concentration of at least one of sorbitol, 1,2-butanediol, and glycerol in the raw product, one or both of (i) the hydrogenation catalytic activity is increased and (ii) at least one of the feed rate and the concentration of the carbohydrate in the feed is decreased.

18. The process of claim 10 wherein the process uses hydrogenation catalyst withdrawn from or intended to be used in a larger reaction zone for evaluating hydrogenation catalytic activity.

19. The process of claim 10 wherein the tracer precursor is added to trouble shoot the process.

20. The process of claim 10 wherein the tracer precursor comprises methylethylketone and the tracers comprise methylethylketone and iso-butanol.

* * * * *